United States Patent [19]
Bennett

[11] Patent Number: 5,195,531
[45] Date of Patent: Mar. 23, 1993

[54] ANESTHESIA ADEQUACY MONITOR AND METHOD

[76] Inventor: Henry L. Bennett, 1006 Bienville, Davis, Calif. 95616

[21] Appl. No.: 663,434

[22] Filed: Mar. 1, 1991

[51] Int. Cl.$^5$ .............................................. A61B 5/04
[52] U.S. Cl. .................................... 128/733; 128/741
[58] Field of Search ............... 128/733, 731, 744, 745, 128/741, 639, 640, 641, 642, 643, 644

[56] References Cited

U.S. PATENT DOCUMENTS

| | | | |
|---|---|---|---|
| 2,902,030 | 9/1959 | Kennedy et al. | 128/733 |
| 3,774,593 | 11/1973 | Hakata et al. | 128/733 |
| 3,946,723 | 3/1976 | Servos | 128/733 |
| 4,448,203 | 5/1984 | Williamson et al. | 128/733 |

FOREIGN PATENT DOCUMENTS 2113846 8/1983 United Kingdom .

OTHER PUBLICATIONS

Edmonds, H. L. et al. "Objective Assessment of Opioid Action by Facial Muscle SEMG" Prog. Neuro-Psychopharmacol & Biol. Psychiat. 22:727-738 (1988).
Paloheimo, M. "Assessment of Anaestetic Adequacy with Upper Facial and Abdominal Wall EMG" Eur. J. Anesthiol. 6:111-119 (1989).
Edmonds, H. L., et al. "Quantitative Surface EMG in Anesthesia and Critical Care" Int. J. Clin. Monitoring and Computing 3:135-145 (1986).
Richie, G. et al. "A Microcomputer Based Controller for Neuromuscular Block During Surgery" Annals of Biomed. Engr. 13:3-15 (1985).
Nielsen, T. A., et al., "Effects of Dream Reflection on Waking Affect: Awareness of Feelings, Rorschach Movement, and Facial EMG" Sleep 12(3):277-286 (1989).
Chang, T., et al., "Continuous Electromyography for Monitoring Depth of Anesthesia" Anesth. Analg. 67:521-5 (1988).
Tammisto, T. et al. "Assessment of Neuromuscular Block Eur. J. Anaesthesiol." 5:1-8 (1988).

Primary Examiner—Max Hindenburg
Assistant Examiner—Guy V. Tucker
Attorney, Agent, or Firm—Bernhard Kreten

[57] ABSTRACT

The anesthesia adequacy monitor measures the level of consciousness of a patient as distinguished from merely the physical paralysis of the patient. Sensors attached to the patient's face measure the micro-expression the patient is exhibiting which is normally undetectable by even a trained observer. This device amplifies the patient's expression and thereby provides both a quantative and a qualitative measure of the patient's reactions to various stimuli during apparent unconsciousness. A display is provided giving an operator a readily discernable representation of the patient's awareness. An artifact detector further enhances the device's utility by filtering out unwanted anomalies from the monitor's output. During surgery, this device can be used to maintain an adequate level of patient awareness while the patient is under anesthesia. After an event resulting in apparent unconsciousness, this device can provide a measure of the patient's true level of awareness. In this way, patient comfort is maximized and patient recovery time is minimized.

39 Claims, 4 Drawing Sheets

ANESTHESIA ADEQUACY MONITOR AND METHOD

FIELD OF THE INVENTION

The following invention relates to devices which measure the clinical condition of a patient under anesthesia during surgery and methods for determining the adequacy of the anesthesia. Specifically, this device measures the level of consciousness of the patient as opposed to merely the level of muscle paralysis. This device provides information to an administrator of anesthesia which helps the administrator to improve patient comfort and safety during surgery.

BACKGROUND OF THE INVENTION

Currently, there is no adequate monitor for noting the depth of unconsciousness of a patient under anesthesia. Rather, heart rate and blood pressure data along with response to surgical stimulation are used to merely infer consciousness. While heart rate and blood pressure can change, these changes are often unrelated both conceptually and empirically to changes in states of unconsciousness and responsiveness within the central nervous system which can provide a better indicator.

Most patients receive muscle relaxants during major surgery. In very special circumstances, which are not easily predicted, patients who are receiving potent muscle relaxants are at risk of remaining conscious of their surroundings during surgery even when receiving some anesthesia. The patients actually feel the pain of the operation but are unable to respond and communicate the pain to the medical team because of the muscle relaxant's effect. When this occurs it can be a horrendous experience because of the helplessness and the some times permanent changes it can bring about within the patient. The changes brought about in the patient are mostly because this aware state is undetected by the anesthesiologists and surgeons in the room by having been masked by the muscle relaxant. This state can and does occur with surprising frequency.

The ideal anesthetic is one in which the patient is comfortable throughout the procedure and emerges unaware of the operation procedure. Although this does happen, there has been no reliable indicator to the anesthesiologist as to when it is happening. The "art" of clinical anesthesia is certainly part of this system, but it is also unreliable as there are occasional failures.

The problem is serious enough that attempts at monitoring the level of consciousness of the patient have been made over the years. The electroencephalogram was the first logical system employed but has been found to be completely inadequate for various reasons.

Secondly, another monitor has appeared on the market called the lower esophageal contractility monitor. While enjoying certain advantages, the lower esophageal contractility monitor is being shown in the empirical literature to be inadequate as an accurate and reliable guide to the state of central nervous system activity.

Thirdly, a device using a surface electromyogram attached to the Frontalis muscle of a patient's face has had some success at measuring patient awareness. However, because this device only senses one facial muscle group, the information received is neither as accurate nor as reliable as the device of this application. Thus, the desire for advances in medical care as well as issues of litigation and medical ethics speak to a need to understand more about the central nervous system in terms of both consciousness and unconsciousness, effective responses to pain, and general assessment of "comfort".

The applicant's device provides a consciousness monitor which substantially advances the prior art in a new and useful way by analyzing the micro-expressions of the anesthetized patient. The device provides an accurate and reliable indictor of the consciousness of the patient and the adequacy of the anesthesia. It has been discovered by applicant that a patient's recovery from an operation can be correlated directly to the level of unconsciousness attributable to the anesthesia administered The following prior art references reflect the state of the art of which applicant is aware and are included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

UK Published Patent Application GB 2 113 846, Filed by Instumentarium Oy (Finland), inventors Rantala, B., et al., publication date Aug. 10, 1983

Ritchie, G., et al., A Microcomputer Based Controller for Neuromuscular Block During Surgery, *Annals of Biomed. Eng.* 13:3-15 (1985)

Nielsen, T. A., et al., Effects of Dream Reflection on Waking Affect: Awareness of Feelings, Rorschach Movement, and Facial EMG, *Sleep* 12 (3) :277-286 (1989)

Chang, T., et al., Continuous Electomyography for Monitoring Depth of Anesthesia, *Anesth Analg.* 67:521-5 (1988)

Tammisto, T., et al., Assessment of Neuromuscular Block: Comparison of Three Clinical Methods and Evoked Electromyography, *Eur. J. Anaesthesiol.* 5:1-8 (1988)

Edmonds, H. L., et al., Objective Assessment of Opioid Action by Facial Muscle Surface Electromyography (SEMG), *Prog. Neuro-Psychopharmacol. & Biol. Psychiat.* 22:727-738 (1988)

Schwilden, H., Surveillance et Conduite de l'Anesthesie a l'Aide de l'EEG, des Potentiels Evoques, de l'EMG du Muscle Frontal ou du Monitorage de la Contractilite Oesophagienne, *Ann. Fr. Anesth. Reanim.* 8:162-166 (1989)

Paloheimo, M., Assessment of Anaesthetic Adequacy With Upper Facial and Abdominal Wall EMG, *Eur. J. Anaesthiol.* 6:111-119 (1989)

Edmonds, H. L., et al., Quantitative Surface Electomyography in Anesthesia and Critical Care, *Int. J. Clin. Monitoring and Computing* 3:135-145 (1986)

The Patent to Rantala teaches the use of a device for measuring the depth of anesthesia which combines a surface electromyogram attached to a facial muscle with an electroencephalogram and an electromyogram attached to a patient's hand. While this application does sense the facial muscle activity, it interprets the activity directly rather than using surface electromyogram readings to determine a facial expression corresponding to the consciousness of the patient, as does the applicant's device. Furthermore, the applicant's device uses an array of surface electromyograms providing a more accurate representation of a patient's facial expression, and hence a more accurate representation of the patient's consciousness state.

The article by Chang is of interest in that it also uses a surface electromyogram attached to a facial muscle group and electroencephalogram data during surgery. However, the method taught in this article was designed to effectively administer anesthesia and provided no method for monitoring the consciousness of the patient for patient comfort as does the invention described hereinbelow.

The article by Edmonds describes a device which attaches a surface electromyogam to a single facial muscle for the purpose of determining a patient's consciousness.

The device of this application more effectively achieves this purpose by sensing plural facial muscle groups simultaneously providing a more accurate and reliable indication of the patient's consciousness through sensing the facial expression of the patient. Furthermore, the device of this application provides a method for filtering out unwanted data from the sensors and a clearer method of consciousness display.

The remaining prior art listed above diverge more starkly from the present invention. By actually detecting the expression of the patient under anesthesia the applicant's device provides a measure of anesthesia adequacy which is not contemplated by any existing devices or methods.

SUMMARY OF THE INVENTION

The applicant's device senses patient awareness essentially by measuring the micro-expression which exists on the patient's face even when the patient appears to be unconscious. An array of surface electromyograms are used to quantify the magnitude of the facial micro-expression and qualify the nature of the expression (i.e. solitude, distress, pain, etc.). Each surface electromyogram has an electrode attached to the face of the patient where it can measure the activity of a single facial muscle group. Experiment has shown that four surface electromyograms attached to the Corrugater, Zygomatic, Frontalis and Masseter muscle groups provide the best indication of the patient's expression.

Once the four surface electromyograms have created electronic signals representing each facial muscle group, the signals are analyzed by a computer algorithm. The algorithm is tailored to determine the quantity and quality of the facial expression from the relative voltage levels among the separate signals sent from the different facial muscle groups. The algorithm outputs a signal which represents the composite facial expression which the patient is currently experiencing. This combined signal representing the patient's facial expression is then sent to a display device.

In one version of the invention, the display graphically represents the magnitude of the facial expression. An operator of the equipment can monitor the magnitude of the facial expression and use it as an indicator of the tonus level of facial muscle activity, and thus the adequacy of the anesthesia. In another version, the display may be in the form of an illustrated face with the expression sensed by the surface electromyograms represented on the display. The display may be magnified to allow the user to determine the patient's expression and analyze it both qualitatively and quantitatively.

An artifact detector and signal filter may be interposed between the facial muscle sensors and the computer algorithm. During surgery, a surgeon often uses an electrical cauterizing device. This device causes stimulation of the patient's facial muscles regardless of the level of patient consciousness. Use of this cauterizing device contaminates the output of this invention by causing anomalies in the data measured by the surface electromyograms. These artifacts may be detected by a device attached to the electrical cauterizer itself and also connected to the surface electromyogram signal before it enters the computer algorithm. The artifact detector can then quantify the magnitude of the disturbance caused by the artifact and activate the filter to filter out the unwanted portion of the signal representing the artifact. In this way, the signal is purified, improving the accuracy of the output.

The applicant's device may be incorporated into a method of monitoring patient awareness during surgery. The anesthesiologist may monitor the facial expression display for indications of patient consciousness. When the anesthesiologist detects an undesirable consciousness level, the anesthesiologist may adjust the level of anesthesia dosage to adjust the patient's sensitivity to external stimulus. The anesthesiologist may monitor the facial expression display to determine the response the patient is having to this altered dose of anesthesia and make appropriate further adjustments. As a result, the patient is more likely to not only have no memory of the events taking place during surgery, but also a smoother less distressful recovery from surgery.

OBJECTS OF THE INVENTION

Accordingly, it is a primary object of the present invention to provide a device which accurately detects patient's consciousness during surgery.

Another object of the present invention is to provide a patient consciousness device which has an easy to understand display.

Another object of the present invention is to provide an anesthesia adequacy monitor that filters out the effect of unwanted artifacts from the output signal.

Another object of the present invention is to accurately measure the patient's facial expression through surface electromyography of facial muscles.

Another object of the present invention is to provide a device which gives a quantitative and a qualitative indication of patient comfort.

Another object of the present invention is to provide a device which can measure the facial expression of a patient under anesthesia and amplify it for observation by physicians during surgery.

Another primary object of the present invention is to provide a method for maintaining patient's unconsciousness during surgery.

Another object of the present invention is to provide a method for reducing the likelihood that a patient will remember feeling anything during a medical surgery.

Another object of the present invention is to provide a method of maintaining patient unconsciousness which involves a simple procedure for providing useful data to the anesthesiologist.

Another object of the present invention is to provide a method for reducing the awareness of the patient of events which occur during surgery.

Viewed from a first vantage point it is an object of the present invention to provide a device for monitoring the consciousness of a patient under anesthesia including a sensor of facial muscle activity in the patient, a micro computer for interpreting the patient's awareness from said sensor, and a display for accurately communicating to an anesthesiologist the level of patient awareness.

Viewed from a second vantage point it is an object of the present invention to provide a device for informing an anesthesiologist of the level of consciousness of a patient under anesthesia through detection of the patient's facial expression including an array of facial muscle sensors strategically located on the patient, a signal processing system capable of converting a first signal representing raw sensor output from the sensors into a second signal representing the patient's facial expression and an output device driven by said second signal.

Viewed from a third vantage point it is an object of the present invention to provide a method for maintaining an appropriate level of patient consciousness under anesthesia including the steps of configuring an array of sensors on a patient's face, creating a signal with the sensors, processing the signal created by the sensors, displaying the signal for viewing by an anesthesiologist, anesthetizing the patient with an initial dosage of anesthetic to create muscle relaxation and a desired level of consciousness, and controlling the patient's level of consciousness.

Viewed from a fourth vantage point it is an object of the present invention to provide a method for monitoring a patient's level of consciousness through detection of the patient's facial expression including the steps of attaching facial muscle sensors to the patient's face, forming an electronic signal from the facial muscle sensor's input, transforming the electric signal into a pictorial display of a face with the facial expression of the patient superimposed thereon, and magnifying said signal such that the facial expression experienced by the patient is easily noticeable by an operator.

DESCRIPTION OF THE DRAWING FIGURES

DESCRIPTION OF PREFERRED EMBODIMENT

Figure 1:
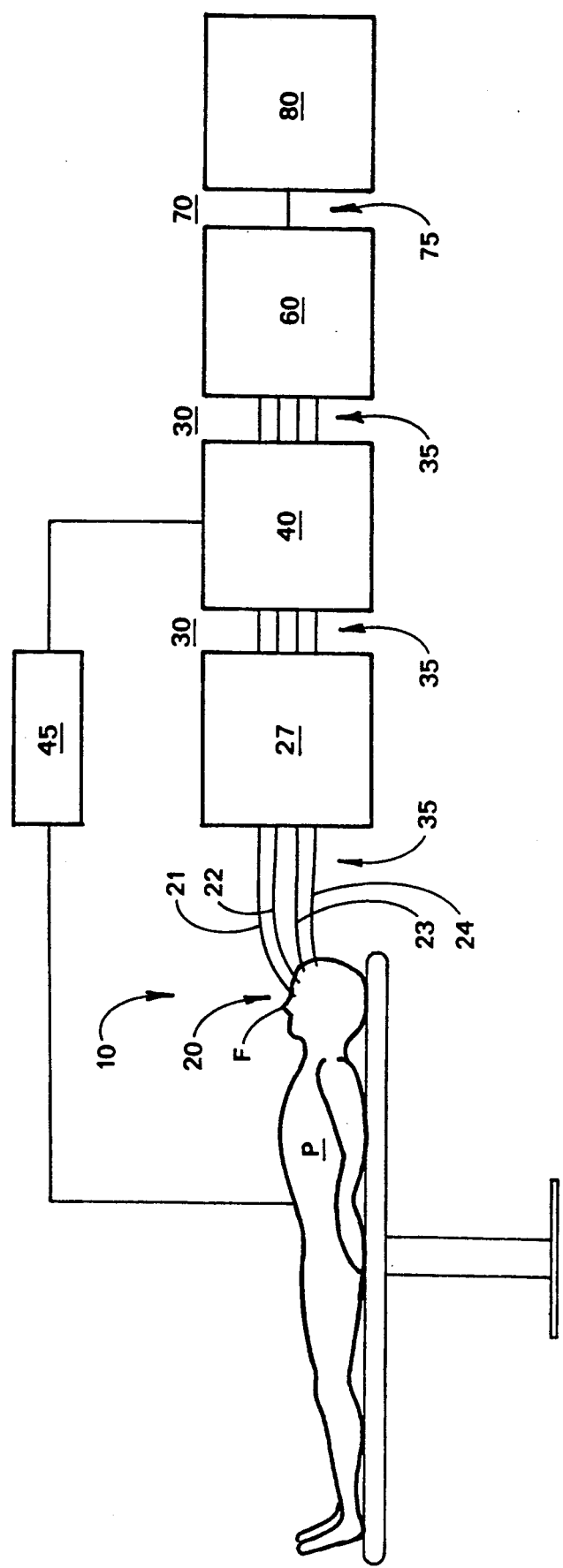
FIG. 1 is a block diagram representing the relationships of the elements of the device of this application.

Referring now to the drawings wherein like numerals represent like components throughout, numeral 10 represents an anesthesia adequacy monitor. The monitor 10 connects to muscles of a face F of a patient P undergoing surgery. An operator of the monitor 10 observes a display 80 to determine the awareness of the patient P.

In essence, the monitor 10 consists of a sensor array 20 (FIG. 3) attached to the face F of a patient P through a plurality of electrodes 26 having a base 28 which attaches to the face F. The sensor array 20 detects the level of muscle tonus of the muscles of the patient's face F and creates a first signal 35 (FIGS. 1 and 2) representing the muscle tonus. The signal 35 is transported through a first signal conduit 30 to a processor computer 60. The computer 60 uses the first signal 35 as input in creating a second signal 75 representing the facial expression of the patient P. The second signal 75 is transported through a second signal conduit 70 to the display 80. The display 80 then displays output data representing the patient's facial expression to an operator.

Figure 2:
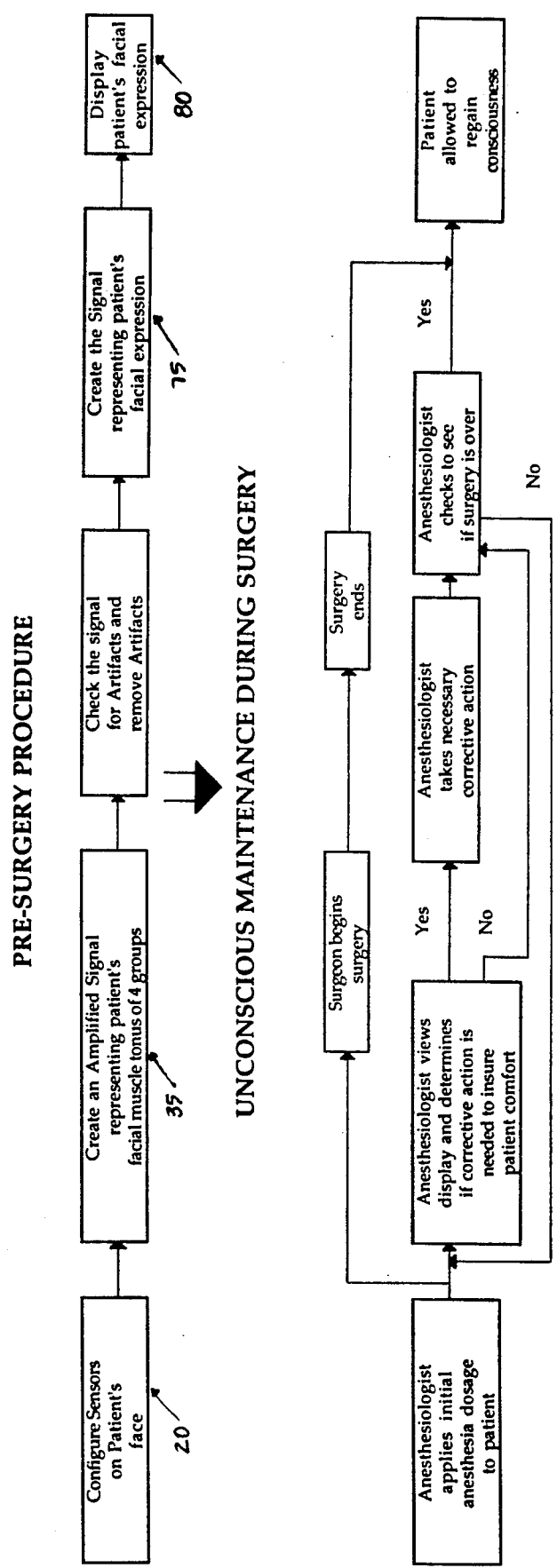
FIG. 2 is a block diagram representing the relationships of the steps of the method of this application.
Figure 3:
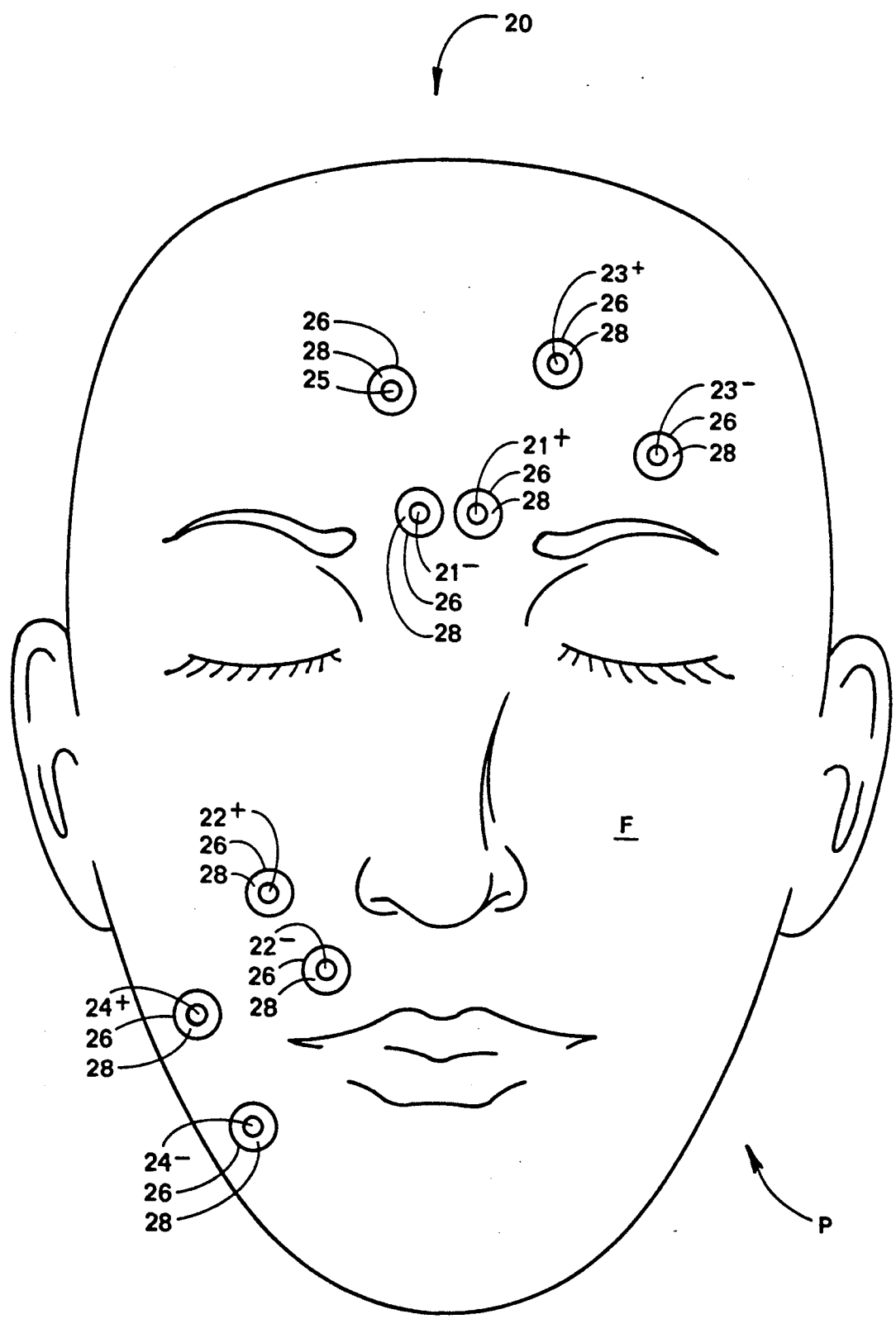
FIG. 3 is a plan view of a portion of the device in place on a person's face.

More specifically and as shown in FIG. 3, the sensor array 20 is composed of a first sensor 21, a second sensor 22, a third sensor 23, a fourth sensor 24 and a ground sensor 25. The sensors 21, 22, 23, 24 are attached to the Corrugator, Zygomatic, Frontalis and Masseter facial muscle groups, respectively. Each non-ground sensor 21, 22, 23, 24 has two electrodes 26. One electrode 26 from each sensor 21, 22, 23, 24 has a positive bias and is affixed to the face F where it can accurately measure tonus in the corresponding facial muscle group. Another electrode 26 from each sensor 21, 22, 23, 24 has a negative bias and is affixed to the face F where it can accurately measure tonus in the corresponding muscle group. The magnitude of voltages between the two electrodes 26 of each non-ground sensor 21, 22, 23, 24 compared with the ground sensor 25 determines values constituting the first signal 35. The initial signal, which is generated by the sensors 21, 22, 23, 24 is passed through a pre-amplifier 27, (FIG. 1), enhancing the signal for further manipulation. The output signal of the pre-amplifier 27 is the first signal 35 (FIG. 2). Preferably, the sensor array 20 is of a type referred to in the art as a surface electromyogram.

In an alternative embodiment, the sensor array 20 may be composed of the first sensor 21 attached to the corrugator facial muscle group and the third sensor 23 attached to the frontalis facial muscle group. Output from these sensors 21, 23 are then processed by the pre-amplifier 27 creating the first signal 35.

Once the first signal 35 is created, it is transmitted to the computer 60 through a first signal conduit 30. The first signal 35 represents four separate values for each of the four facial muscle groups being monitored.

A first algorithm within the computer 60 interprets the four values of the signal 35 and determines the facial expression that the signal 35 represents. The first algorithm then creates the second signal 75 which represents the facial expression of the patient P.

The second signal 75 is transmitted through the second signal conduit 70 to the display 80. A variety of different outputs from the display 80 are contemplated.

Preferably, the display 80 shows a graphic depiction of a generic human face with indicia of the comfort and awareness of the patient P superimposed thereon. For instance, when the patient is fully unconscious the display will show a calm face. When the patient is more aware the display will show a more tortured facial expression. The first signal 35 and second signal 75 are magnified by the preamplifier 27 and thus the display 80 clearly represents the patient's facial expression where direct viewing of the patient P reveals an apparently totally unconscious state.

Figure 4:
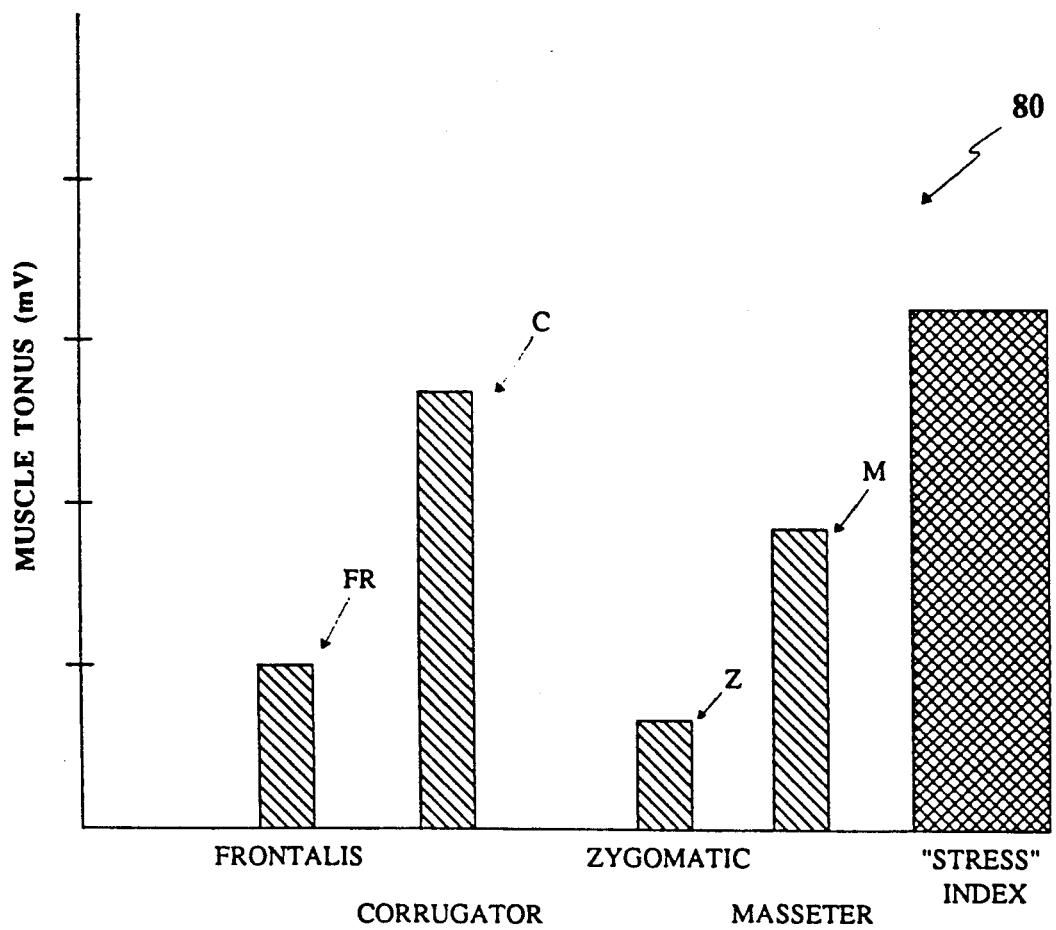
FIG. 4 is a plan view of various possible outputs for display of the device of this application.

In an alternative embodiment, the display 80 represents graphically the level of facial muscle tonus, either for each muscle group separately, for all of the facial muscles combined, or for a combination of muscles using a second algorithm to create a "stress" index (FIG. 4).

This second algorithm for determining the "stress" index uses the following formula:

$$[C+M]-[FR+Z]=\text{"Stress"}$$

Where:
C is the muscle tonus of the Corrugator muscle,
M is the muscle tonus of the Masseter muscle,
FR is the muscle tonus of the Frontalis muscle,
Z is the muscle tonus of the Zygomatic muscle, When the sensor array 20 is composed of only the first sensor 21 and the third sensor 23, the second algorithm is still capable of determing a modification of the "stress" index. The formula becomes:

C−FR="Stress"

An artifact detector 40 (FIG. 1) may be interposed between the pre-amplifier 27 and the computer 60 along the first signal conduit 30. The artifact detector 40 purifies the first signal 35. Particularly, often during surgery a surgeon uses an electric cauterizing device 45. When this device is used, some electric current flows through the patient P causing an anomaly in the readings of the sensor array 20.

The detector 40 is connected on one end to the cauterizing device 45, or other artifact generator, and on another end to the first signal conduit 30. When an artifact is detected by the detector 40, the detector 40 then filters out the portion of the first signal 35 representing only the artifact. The resultant first signal 35 is more truly representative of the facial muscle tonus of the patient P.

In use and operation, the anesthesia adequacy monitor 10 may be used by an anesthesiologist or other qualified operator to maintain patient unconsciousness during surgery as suggested in FIG. 2. Initially, the anesthesiologist configures the sensor array 20 on the face F of the patient P. A base line reading may then be established. The patient P is then given anesthesia appropriate for the circumstances. The anesthesiologist may then monitor the display 80 to determine the patient's level of consciousness as reflected by changes in muscle tonus. Once the surgery begins, the anesthesiologist may use the display 80 to monitor the magnitude of the patient's response to what otherwise would be objectively painful surgical stimulus. If the display 80 demonstrates an unacceptably high level of awareness, the anesthesiologist may administer more anesthesia or take other corrective action. If the display 80 demonstrates an unacceptably low level of awareness, other corrective measures may be taken. In this way, the patient's comfort can be maximized and the patient's reaction to the surgical procedure and therefore recovery time can be minimized.

In an alternative embodiment, the anesthesia adequate monitor 10 may be used with a patient P who has suffered injury and is experiencing a diminished level of consciousness. Qualified personnel may attach the monitor 10 to the face F of the patient P and then monitor the display 80 to determine the "awareness" of the patient P. Used in this way, the anesthesia adequacy monitor 10 becomes a monitor of the level of patient consciousness during treatment and recovery as opposed to during surgery.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A device for monitoring the consciousness of a patient under anesthesia comprising, in combination:
   an array of facial muscle sensors adapted to be strategically located on the patient to generate signals representing the activity of at least two facial muscles, said muscles being responsible for eliciting distinctive patterns of facial expressions,
   a processor for interpreting the patient's awareness from comparison of measurements made by said sensors and operatively coupled to said sensors, wherein said processor includes a means for determining the facial expression of the patient by interpreting a signal created by said sensors, and
   a display with means receiving output from said processor for accurately communicating to an anesthesiologist the level of patient awareness and therefore consciousness;
   whereby the anesthesiologist may monitor the patient's consciousness and take corrective action to improve patient comfort when indicated.

2. The monitoring device of claim 1 wherein said sensors are surface electromyograms adapted to be physically attached to the patient's face in positions allowing monitoring of multiple facial muscles.

3. The monitoring device of claim 2 wherein a signal pathway is interposed between said sensors and said processor whereby a signal originating in said sensor may be transported to said processor.

4. The monitoring device of claim 3 wherein said processor is a microcomputer which is programmed to determine the facial expression of the patient by interpreting said signal created by said sensors and include means to amplify said signal between said sensors and said processor.

5. The monitoring device of claim 4 wherein a signal filter is interposed between said sensors and said microcomputer for filtering out artifacts from said signal which represent muscle contraction caused by a known external electric stimulus device, said signal filter enabled by the electric stimulus device, whereby the signal may accurately represent the patient's facial response to nerve sensation without distortion caused by the electric stimulus device used on the anesthetized patient during an operating procedure.

6. The monitoring device of claim 5 wherein said sensors include plural surface electromyograms all of which combine to create said signal for input to said microcomputer, whereby a more accurate representation of the patient's expression may be determined.

7. The monitoring device of claim 6 wherein said surface electromyograms are adapted to be attached to Corrugator and Frontalis facial muscles, such that detailed patient awareness analysis may be performed.

8. The monitoring device of claim 6 wherein said surface electromyograms are adapted to be attached to Corrugator, Zygomatic, Frontalis, and Masseter facial muscles.

9. A consciousness detector for informing an anesthesiologist of the level of consciousness of a patient under anesthesia through detection of the patient's facial expression comprising, in combination:
   an array of facial muscle sensors adapted to be strategically located on the patient and generating signals relating to measurements of the activity of at least two facial muscles, said muscles being responsible for eliciting distinctive patterns of facial expressions,
   a signal processing system for interpreting the patient's awareness coupled to said sensor array said signal processing system including a means for comparing said sensor signals, said signal processing system determining the facial expression of the patient by interpreting said sensor signals and converting a first signal representing raw sensor output from said sensors into a second signal representing output from said signal processing system reflective of the patient's facial expression, and a display device operatively driven by said second signal;

whereby when an unexpectedly high or unexpectedly low level of patient consciousness is detected the anesthesiologist may take corrective action.

10. The consciousness detector of claim 9 wherein an artifact detector and signal compensator are interposed between said array of sensors and said signal processing system such that when external electrical or physical forces are applied to the patient under anesthesia said artifact detector and signal compensator filters out the direct effect of these external forces on the patient's facial muscles and the indirect effect on said first signal; whereby said first signal is shielded from distortion providing a more accurate representation of the patient's facial expression in response to nerve stimulation.

11. The consciousness detector of claim 10 wherein said array of sensors is formed from a plurality of surface electromyographs.

12. A consciousness detector for informing an anesthesiologist of the level of consciousness of a patient under anesthesia through detection of the patient's facial expression comprising, in combination:

an array of facial muscle sensors adapted to be strategically located on the patient, a signal processing system coupled to said sensor array capable of converting a first signal representing raw sensor output from said sensors into a second signal representing output from said signal processing system reflective of the patient's facial expression, and a display device operatively driven by said second signal;

whereby when an unexpectedly high or unexpectedly low level of patient consciousness is detected the anesthesiologist may take corrective action, wherein an artifact detector and signal compensator are interposed between said array of sensors and said signal processing system such that when external electrical or physical forces are applied to the patient under anesthesia the direct effect of these external forces on the patient's facial muscles and the indirect effect on said first signal is filtered out of said first signal; whereby said first signal is shielded from distortion providing a more accurate representation of the patient's facial expression in response to nerve stimulation, wherein said array of sensors is formed from a plurality of surface electromyographs, wherein said display device is a monitoring screen which displays a human face with indicia communicating the expression represented by said second signal; whereby the patient's expression may be monitored providing the anesthesiologist with an indication of the patient's level of consciousness.

13. The consciousness detector of claim 12 wherein said surface electromyographs of said array are adapted to be attached to the Corrugator and Frontalis facial muscles.

14. The consciousness detector of claim 12 wherein said surface electromyographs of said array are adapted to be attached to the Corrugator, Zygomatic, Frontalis and Masseter facial muscles.

15. A method for maintaining an appropriate level of patient unconsciousness under anesthesia, the steps including:

configuring an array of at least two sensors on a patient's face, creating a signal with the sensors, processing the signal created by the sensors to determine what facial expression the signal represents by comparing the signals from different sensors, the signals being reflective of the patient's facial muscle tonus, displaying the processed signal for viewing by an anesthesiologist on a display, anesthetizing the patient with an initial dosage of anesthetic to create muscle relaxation in a desired level of consciousness, and controlling the patient's level of consciousness.

16. The unconsciousness maintenance method of claim 15 wherein said controlling step includes:

monitoring the display to determine the patient's level of consciousness through subtle changes in the patient's facial expressions resulting from stimuli, administering consciousness correcting means to the patient to correct the patient's actual level of consciousness to the desired level of consciousness, and maintaining the patient's level of consciousness by repeating said monitoring step and said administering step.

17. The unconsciousness maintenance method of claim 16 wherein said configuring step includes:

selecting appropriate facial muscle sensors, attaching the sensors to appropriate muscles on the patient's face, and sending the signal created by the sensors to a signal processor.

18. The unconsciousness maintenance method of claim 17 wherein said processing step includes:

detecting and filtering out artifacts unrepresentative of the patient's expression through steps of:

detecting when an artifact generating device is in operation quantifying the artifact generating device's effect on the signal as measured by the facial muscle sensors, and subtracting from the signal the portion caused by the artifact;

whereby the signal is left unaffected by the artifact.

19. A method for monitoring a patient's level of consciousness through detection of a patient's facial expression the steps including:

attaching facial muscle sensors to the patient's face, forming an electronic signal from the facial muscle sensor's input, transforming the electric signal into a pictorial display of a face with the facial expression of the patient superimposed thereon, and magnifying the signal such that the facial expression experienced by the patient is easily noticeable by an operator.

20. The unconsciousness monitoring method of claim 19 wherein said attaching step includes:

placing a sensor on the Corrugator muscle,
placing a sensor on the Zygomatic muscle,
placing a sensor on the Frontalis muscle, and
placing a sensor on the Masseter muscle.

21. An anesthetized patient awareness and facial expression monitor comprising in combination:

an array of facial muscle sensors adopted to be strategically located on the patient to generate signals representing the activity of at least two facial muscles, said muscles being responsible for eliciting distinctive patterns of facial expressions;

signal processing means including awareness detection means and stress detection means, said signal processing means connected to said sensors and utilizing output from said sensors; wherein said signal processing means includes a means for determining the facial expression of the patient by comparing the signals representing the activity of said at least two facial muscles, and display means operatively coupled to receive the output from said sensors for communicating patients awareness and stress;

whereby an anesthetized patient may be monitored during surgery to determine the adequacy of the anesthesia through analysis of the patient's awareness and stress.

22. The monitor of claim 21 wherein said stress detection means of said signal processing means utilizes quantitative data from said sensors to determine both the existence of and magnitude of the stress level of the patient.

23. A method for monitoring the depth and degree of anesthetization of a patient, the steps including:

segregating into two groups muscles of the patient based on the muscle's ability to respectively reflect pain or the absence of pain by change in muscle tonus, monitoring the activity of at least one muscle from each group, establishing a baseline for each muscle monitored prior to performing an operatory procedure, comparing the muscles monitored from each group for relative changes correlative of the patient experiencing pain during the operatory procedure said comparing step including quantifying muscle tonus values for each monitored muscle and calculating a difference between values of at least one muscle from each group to establish a measure of patient pain recognition, and displaying the comparison.

24. The method of claim 23 including the step of modifying the anesthetic administered to the patient in response to anomalies in the comparison displayed by said displaying step.

25. The method of claim 23 wherein said monitoring step includes monitoring the activity of at least one facial muscle.

26. The method of claim 23 wherein said monitoring step includes monitoring the activity of at least one facial muscle for each group.

27. The method of claim 23 wherein said comparing step includes recognizing a difference between muscles from both groups.

28. The method of claim 23 wherein said monitoring step includes monitoring the activity of the corrugator and frontalis facial muscles.

29. The method of claim 23 wherein said monitoring step includes monitoring the activity of the corrugator, frontalis, masseter and frontalis facial muscles.

30. A method for monitoring the depth and degree of anesthetization of a patient, the steps including:

segregating into two groups muscles of the patient based on the muscle's ability to respectively reflect pain or the absence of pain by change in muscle tonus, monitoring the activity of at least one muscle from each group, establishing a baseline for each muscle monitored prior to performing an operatory procedure, comparing the muscles monitored from each group for relative changes correlative of the patient experiencing pain during the operatory procedure;

displaying the comparison; and wherein said comparing step includes calculating a ratio for each monitored muscle and calculating a difference between values of at least one muscle from each group to establish a measure of patient pain recognition.

31. The method of claim 30 wherein said monitoring step includes monitoring the activity of the corrugator and frontalis facial muscles.

32. The method of claim 30 wherein said monitoring step includes monitoring the activity of the corrugator, frontalis, masseter and frontalis facial muscles.

33. An anesthesia monitor for measuring the depth and quality of patient anesthetization, comprising, in combination:

at least one first sensor adapted to be operatively coupled to at least one patient's muscle selected from a first group of muscles having a tonus which changes when a patient experiences pain, at least one second sensor adapted to be operatively coupled to at least one patient's muscle selected from a second group of muscles having a tonus which changes when a patient experiences the absence of pain, signals emanating from said sensors, a signal processing means receiving said signals from said first sensors and said second sensors, said signal processing means having means to initialize said signals before said patient undergoes an operatory procedure, said signal processing means having means to measure changes in said signals, said signal processing means having means to compare said signals from said first sensors with said signals from said second sensors reflective of changes in the tonus and for determining the facial expression of the patient from said comparison; and a display means operatively coupled to said signal processing means for communicating the depth of the patient's anesthetization;

whereby a user may determine the depth and quality of patient anesthetization.

34. The monitor of claim 33 wherein at least one of said sensors from either said first group or said second group is a facial muscle sensor, whereby muscle activity related to facial micro-expressions may be monitored.

35. The monitor of claim 33 wherein at least one of said sensors from each said group is a facial muscle sensor, whereby muscle activity related to facial micro-expressions may be monitored.

36. The monitor of claim 33 wherein said means to compare said signals calculates a difference between changes in muscle tonus values of muscles from each said group.

37. The monitor of claim 33 wherein said means to compare said signals calculates a ratio between changes in muscle tonus values of muscles from each said group.

38. The monitor of claim 33 wherein at least two said sensors are adapted to be operatively connected to muscles including the frontalis facial muscle and the corrugator facial muscle.

39. The monitor of claim 38 wherein at least two sensors are adapted to be operatively coupled to the masseter facial muscle and zygomatic facial muscle, whereby said signal processing means may determine a detailed indication of patient facial expression reflecting the depth and quality of patient anesthetization.

* * * * *